United States Patent
Corcoran et al.

(10) Patent No.: US 9,423,332 B2
(45) Date of Patent: Aug. 23, 2016

(54) SYSTEM AND METHOD FOR VALIDATING COMPACTION OF A WORK SITE

(71) Applicant: Caterpillar Inc., Peoria, IL (US)

(72) Inventors: Paul T. Corcoran, Washington, IL (US); Liqun Chi, Peoria, IL (US); Brad L. Holsapple, Metamora, IL (US)

(73) Assignee: Caterpillar Inc., Peoria, IL (US)

( * ) Notice: Subject to any disclaimer, the term of this patent is extended or adjusted under 35 U.S.C. 154(b) by 37 days.

(21) Appl. No.: 14/513,823

(22) Filed: Oct. 14, 2014

(65) Prior Publication Data

US 2016/0103051 A1    Apr. 14, 2016

(51) Int. Cl.
| | |
|---|---|
| *G01N 9/36* | (2006.01) |
| *E01C 3/04* | (2006.01) |
| *E01C 7/00* | (2006.01) |
| *E01C 19/23* | (2006.01) |
| *E02D 1/02* | (2006.01) |
| *E02D 3/02* | (2006.01) |

(52) U.S. Cl.
CPC . *G01N 9/36* (2013.01); *E01C 3/04* (2013.01); *E01C 7/00* (2013.01); *E01C 19/23* (2013.01); *E02D 1/022* (2013.01); *E02D 3/02* (2013.01)

(58) Field of Classification Search
CPC ............ E01C 3/04; E01C 7/00; E01C 19/23; E02D 3/02; E02D 1/022; G01N 9/36
See application file for complete search history.

(56) References Cited

U.S. PATENT DOCUMENTS

| | | | | |
|---|---|---|---|---|
| 4,708,516 A * | 11/1987 | Miller | ....................... | E01C 7/18 404/27 |
| 4,850,712 A | 7/1989 | Abshire | | |
| 5,727,900 A * | 3/1998 | Sandstrom | .............. | G01P 15/18 404/122 |
| 5,787,378 A * | 7/1998 | Schricker | ................ | F16H 61/12 340/438 |
| 6,188,942 B1 * | 2/2001 | Corcoran | .............. | E01C 19/006 701/408 |
| 6,460,006 B1 * | 10/2002 | Corcoran | .............. | E01C 19/228 404/117 |
| 7,483,808 B2 * | 1/2009 | Greiner | ................. | G01M 17/02 33/521 |
| 7,938,595 B2 * | 5/2011 | Potts | ..................... | E01C 19/288 404/84.1 |
| 8,635,903 B2 * | 1/2014 | Oetken | ................... | E01C 19/26 404/83 |
| 2006/0080017 A1 | 4/2006 | Corcoran | | |
| 2007/0150147 A1 * | 6/2007 | Rasmussen | ........... | E01C 19/004 701/50 |
| 2008/0260462 A1 * | 10/2008 | Ackermann | .......... | E01C 19/288 404/124 |
| 2010/0087992 A1 * | 4/2010 | Glee | ..................... | E01C 19/288 701/50 |
| 2010/0129152 A1 | 5/2010 | Taylor | | |
| 2010/0172696 A1 | 7/2010 | Commuri | | |

(Continued)

FOREIGN PATENT DOCUMENTS

WO    WO 2006/027339 A2    3/2006

*Primary Examiner* — Abigail A Risic
(74) *Attorney, Agent, or Firm* — Leydig, Voit & Mayer, Ltd.

(57) ABSTRACT

A system for validating compaction of work material at a work site including a compaction machine. A sensor and a location sensor are associated with the compaction machine. A controller is configured to receive compaction data from the sensor and position data from the location sensor and to determine a structural parameter of the work material based on the compaction data and physical properties of the compaction machine. The controller associates the structural parameter of the work material with the position data. The controller saves structural parameters and associated position data for different locations in the work site and for different layers of work material in the work site and compares the saved structural parameters and associated position data with predetermined structural design criteria for corresponding locations and layers in the work site.

20 Claims, 4 Drawing Sheets

(56) References Cited

U.S. PATENT DOCUMENTS

2012/0107045 A1* 5/2012 DeClerk ............... E01C 19/236
 404/75
2013/0155058 A1 6/2013 Golparvar-Fard et al.
2013/0238305 A1 9/2013 Digiacobbe et al.
2014/0125651 A1 5/2014 Sharp et al.
2015/0167257 A1* 6/2015 Korb ....................... E02D 3/026
 404/76

* cited by examiner

SYSTEM AND METHOD FOR VALIDATING COMPACTION OF A WORK SITE

TECHNICAL FIELD

This patent disclosure relates generally to a method for validating compaction of a works site and, more particularly, to a system and method for validating a state of compaction of a work site using structural criteria.

BACKGROUND

Compacting machines or compactors are commonly used to compact materials (such as soil, gravel, asphalt, landfill trash) to a desired state of compaction at work sites such as mines and landfills as well as construction sites, such as, for buildings, highways, roads, parking lots and other structures. A wide variety of different compacting systems can be used including self-propelled two-wheel and four-wheel compactors, tow-behind systems, and others. Such compacting machines often are passed over the work materials multiple times in order to achieve the desired compaction. Additionally, work sites, such as roads or foundational structures, may have layers of different materials. For example, a road may have pavement overlying a base material that may, in turn, overlie a sub-base material and a sub-grade material. During construction of a road, compaction machines may compact each individual layer to a desired compaction state before starting construction of the next layer.

The capacity of substrate materials to remain stable over time, support loads or serve as a barrier to liquids, as well as other properties, can depend in significant part upon compacting a given material to a certain compaction state. A variety of different methods can be used to determine the compaction state of work materials. For example, simply passing a compactor over a work site will tend to increase the relative compaction state, and thus the stiffness, of the resident material. Thus, to some extent compactor coverage is a metric which has been used to enable an operator or site manager to estimate that a target state of compaction has been achieved.

Other methods involve using the machine to measure compaction in real-time during the compaction process. For example, compaction may be approximated by determining the ability of the work material to support a compaction machine. Current commercial products quantify ground compaction with an index based on machine performance parameters such as motion resistance, or dynamic response in the case of vibratory compactors. However, compaction is quantified as an index value without engineering units. In particular, the systems that measure compaction during the compaction process typically determine a relative state of compaction of the work material. In other words, the systems determine the extent to which the work material has been compacted relative to the maximum compaction capacity or capability of the compaction machine. As a result, the systems may determine that a work material has been compacted to some percentage of the maximum compacting capability of the machine. Such systems do not provide an absolute or empirical measure of the state of compaction, rather the state of compaction is quantified as a unitless measure.

While knowing a relative state of compaction of a work site can be useful information, many compaction projects require a more sophisticated understanding of the actual compaction state of a material. For example, construction design specification criteria are transitioning from empirical and historical quality requirements to more structural quality requirements. Compaction criteria have traditionally been based on soil compaction measures such as density within an acceptable range of soil moisture, but are more recently moving toward more strength based structural criteria such as soil stiffness and/or modulus. Because compaction machines cannot provide such information in real-time, operators may need to perform secondary tests or evaluations at the work site to validate whether the compaction of the material is meeting the design criteria. Some of the secondary tests may require the removal of material from an otherwise finished work surface. In addition, it may be necessary to perform tests at multiple locations to determine whether the desired level of compaction has been uniformly achieved. Another disadvantage of current real-time compaction measurement methods is that a unitless measure of compaction cannot be used for job site modeling purposes, such as to determine the specific compaction of the soil or other material in order to help design roads, building pads or other foundational structures.

U.S. Patent Application Pub. No. 2013/238305 discloses a method for producing a graphical three-dimensional model of a surface of, for example, a paved road or graded soil. This model may then be compared to a reference-surface model. However, the disclosed method does not involve a determination of a state of compaction of the surface.

SUMMARY

In one aspect, the disclosure describes a method for validating compaction of a plurality of layers of work material at a work site. A compaction machine is passed over a first layer of work material at the work site. Compaction data is received from at least one sensor indicative of a state of compaction of the work material as the compaction machine passes over the work material. Position data is received from at least one location sensor indicative of a position of the compaction machine in the work site. A structural parameter of the work material is determined based on the compaction data and the physical properties of the compaction machine as the machine passes. The structural parameter is associated with the position data for the position of the compaction machine in the work site where the compaction data was received. Structural parameters and associated position data are collected across the work site. The structural parameters are saved with the associated position data. The steps are repeated for a second layer of work material at the work site.

In another aspect, the disclosure describes A system for validating compaction of work material at a work site. The system includes a compaction machine and a sensor carried by the compaction machine for generating compaction data indicative of a state of compaction of the work material as the compaction machine passes over the work material. A location sensor is associated with the compaction machine for generating position data indicative of a position of the compaction machine in the work site. A controller is configured to receive compaction data from the sensor and position data from the location sensor and to determine a structural parameter of the work material based on the compaction data and physical properties of the compaction machine. The controller is configured to associate the structural parameter of the work material with the position data for the position of the work machine where the compaction data was received. The controller is configured to save structural parameters and associated position data for different locations in the work site and for different layers of work material in the work site and to compare the saved structural parameters and associated position data with predetermined structural design criteria for corresponding locations and layers in the work site.

In yet another aspect, the disclosure describes a compaction machine for validating compaction of work material at a work site. The compaction machine includes at least one roller drum configured to compact the work material. A sensor is carried by the compaction machine for generating compaction data indicative of a state of compaction of the work material as the compaction machine passes over the work material. A location sensor is associated with the compaction machine for generating position data indicative of a position of the compaction machine in the work site. A controller is configured to receive compaction data from the sensor and position data from the location sensor and to determine a structural parameter of the work material based on the compaction data and physical properties of the compaction machine. The controller is configured to associate the structural parameter of the work material with the position data for the position of the work machine where the compaction data was received. The controller is configured to save structural parameters and associated position data for different locations in the work site and for different layers of work material in the work site and to compare the saved structural parameters and associated position data with predetermined structural design criteria for corresponding locations and layers in the work site.

DETAILED DESCRIPTION

This disclosure generally relates to a system and method for validating the compaction of a work material using data gathered during operation of a compactor machine. The method includes having loose material disposed over a surface, which can be further packed or densified. A compactor or machine travels over the surface of the disposed material, generating forces acting in cooperation with the weight of the machine, which are imparted onto the material compressing it to a state of greater stiffness and density. The compactor may make one or more passes over the surface to provide a desired level of work material compaction. The material being compacted may include asphalt, soil, gravel, sand, landfill trash, concrete, or the like. Hereinafter the material being compacted may be referred to as the work material.

Figure 1:
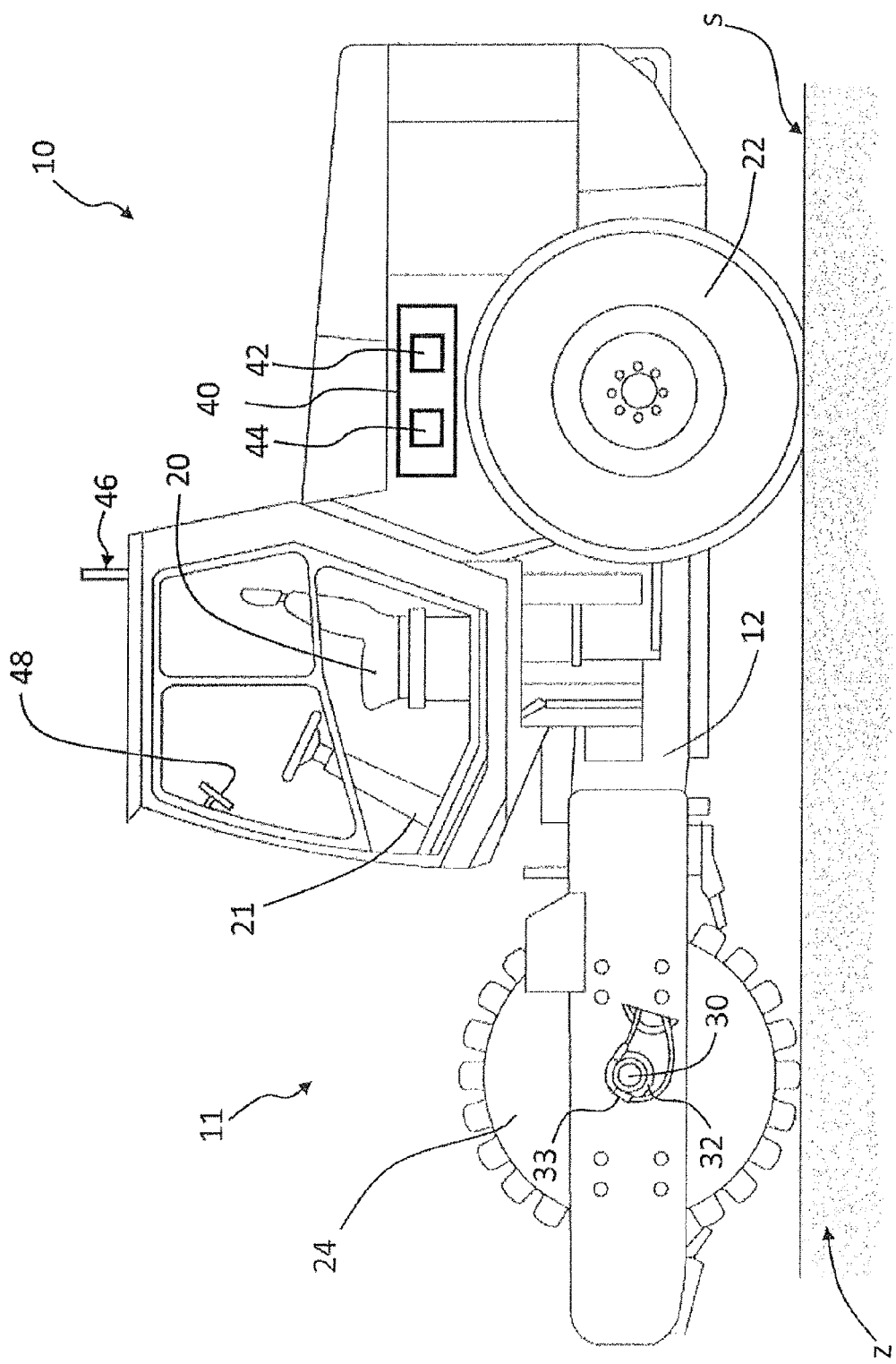
FIG. 1 is a side view of an exemplary compactor system according to one aspect of the disclosure.

FIG. 1 illustrates a side view of an exemplary compactor system 10, according to one aspect of the disclosure. The illustrated compactor system 10 can travel over a surface S compacting a work material Z under its own power and may implement aspects of the disclosure. Other types of compactors are contemplated to implement the disclosed method and system including soil compactors, asphalt compactors, utility compactors, pneumatic compactors, vibratory compactors, self-propelled two-wheel and four-wheel compactors, and tow-behind systems. For example, the disclosed method and system can be applied to four wheel static compactors as well as single and double drum vibratory compactors.

The illustrated compactor system 10 includes a compactor machine 11 that includes a body or frame 12 that interoperatively connects and associates the various physical and structural features that enable the compactor machine 11 to function. These features may include an operator cab 20 that is mounted on top of the frame 12 from which an operator may control and direct operation of the compactor machine 11. Additionally, a steering feature 21 and similar controls may be located within the operator cab 20. To propel the compactor machine 11 over the surface S, a power system (not shown), such as an internal combustion engine, can also be mounted to the frame 12 and can generate power that is converted to physically move the compactor machine 11. One or more other implements (not shown) may be connected to the machine. Such implements may be utilized for a variety of tasks, including, for example, loading, lifting, and brushing, and may include, for example, buckets, forked lifting devices, brushes, grapples, cutters, shears, blades, breakers/hammers, augers, and others.

To enable physical motion of the compactor machine 11, the illustrated compactor machine 11 includes a padfoot drum 24 and rubber tires 22 that are in rolling contact with the surface S. It should be appreciated that machine 11 may have two roller drums for compacting the work material Z, and the drums (or drum in the case of a single drum compactor) may be smooth or equipped with compacting feet, such as a padfoot type design. For reference purposes, the compactor machine 11 can have a typical direction of travel such that the padfoot drum 24 may be considered the forward drum and the rubber tires 22 considered the rear of the machine 10. The padfoot (forward) drum 24 and rubber tires (rearward) 22 can be cylindrical structures that are rotatably coupled to and can rotate with respect to the frame 12. Because of their forward and rearward positions and their dimensions, the padfoot drum (forward) 24 and rubber tires (rearward) 22 support the frame 12 of the compactor machine 11 above the surface S and allow it to travel over the surface S. The padfoot drum (forward) 24 and rubber tires (rearward) 22 are oriented generally transverse or perpendicular to the direction of travel of the compactor machine 11. It should be appreciated that because the compactor machine 11 is steerable, the forward direction of travel may change bearing during the course of operation but can be typically assessed by reference to the direction of movement of the padfoot drum (forward) 24. To transfer motive power from the power system to the surface S, the power system can operatively engage and rotate the rubber tires (rearward) 22 through an appropriate power train. The systems and methods of the disclosure may be used with any machine propulsion and/or power train mechanisms applicable in the art including hydrostatic, electric, or mechanical drives. Additionally, and as noted above, the method and system of the present disclosure are not limited to single or double drum vibratory compactors and, for example, are equally applicable to four wheel static compactors.

To facilitate control and coordination of the compactor machine 11, the compactor machine 11 may include a controller 40 such as an electronic control unit. The controller 40 may utilize various input devices to control the compactor machine 11 and one or more sensors to provide data and input signals representative of various operating parameters of the compactor machine 11 and/or the environment of the work site at which the compactor machine 11 is operating. While the controller 40 is illustrated in FIG. 1 as a single unit, in other aspects the controller 40 may be distributed as a plurality of distinct but interoperating units, incorporated into another component, or located at a different location on or off the compactor machine 11. The term "controller" is meant to be used in its broadest sense to include one or more controllers and/or microprocessors that may be associated with the compactor machine 11 and that may cooperate in controlling various functions and operations of the compactor machine. The functionality of the controller 40 may be implemented in hardware and/or software without regard to the functionality. The controller 40 may rely on one or more data maps relating to the operating conditions and the operating environment of the compactor machine 11 and the work site that may be stored in the memory of controller. Each of these data maps may include a collection of data in the form of tables, graphs, and/or equations.

The controller 40 may be located on the machine 10 and may also include components located remotely from the machine such as at a command center. The functionality of controller 40 may be distributed so that certain functions are performed at the compactor machine 11 and other functions are performed remotely. In such case, the controller 40 may include a communications system such as wireless network system for transmitting signals between the compactor machine 11 and a system located remote from the machine.

Figure 2:
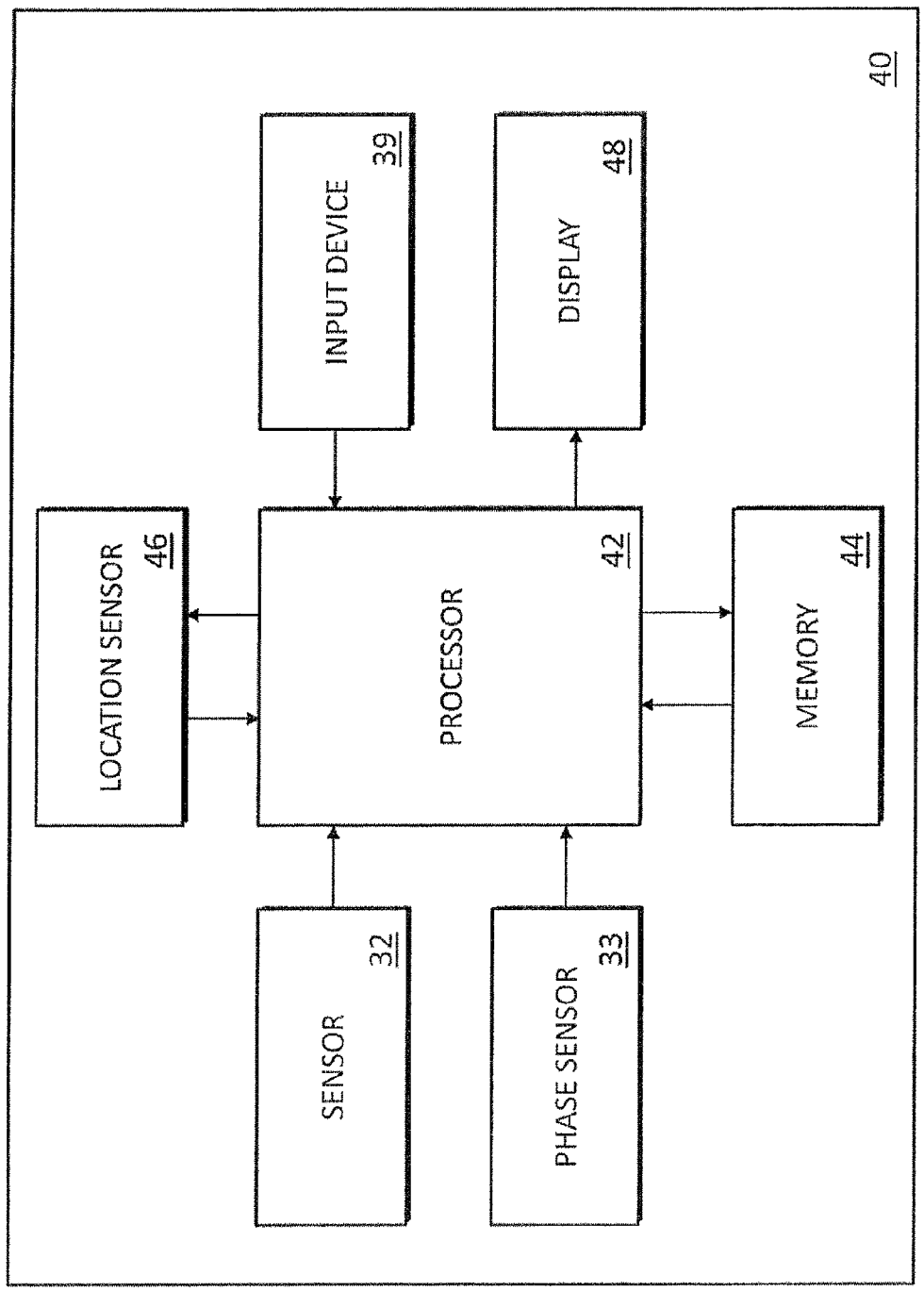
FIG. 2 is a block diagram of an exemplary controller.

FIG. 2 illustrates a block diagram of an embodiment of the components that may comprise the controller 40. The controller 40 may include a sensor 32, a phase sensor 33, an input device 39, a processor 42, a memory 44, a location sensor 46, a display or output 48, and a vibration system (not shown). The main unit of the controller 40 may be located in the operator cab 20 for access by the operator and may communicate with the steering feature 21, the power system, and with various other sensors and controls on the compactor machine 11. The input device 39 may be located on the compactor machine 11 or it may be located remotely. For example, the input device 39 may be a keyboard located in the operator cab 20. Alternatively, the input device 39 may be a mobile device or may be a desktop computer or computer server located at a remote location that communicates with the controller 40 via a communication channel.

The sensor 32 may be configured to sense a parameter from which a structural criteria of the work material Z may be determined. More particularly, the sensor 32 may be configured to generate compaction data indicative of a state of compaction of the work material as the compaction machine 11 passes over the work material. The term "sensor" is meant to be used in its broadest sense to include one or more sensors and related components that may be associated with the compactor machine 11 and that may cooperate to sense various functions, operations, and operating characteristics of the machine. In one embodiment, the sensor 32 may sense a parameter indicative of the acceleration, velocity, displacement, and/or force of a component of the compactor machine 11. The components may include the padfoot drum (forward) 24, the rubber tires (rearward) 22, a roller drum (not shown), the compactor frame 12, or the like. The sensor 32 may include a signal transducer configured to sense a transmitted signal, or component of a transmitted signal. For example, the signal reflected by surface S. In FIG. 1, a single sensor 32 is shown coupled with and resident on padfoot drum (forward) 22. In other embodiments, additional sensors such as a rearward sensor (not shown) associated with rubber tires (rearward) 22 or a rear roller drum, individual sensors located in proximity to the padfoot drum (forward) 24 and/or rubber tires (rearward) 22, or separate sensors for measuring acceleration and/or displacement of the padfoot drum (forward) 24, the rubber tires (rearward) 22, a roller drum, and the compactor frame 12 may be used.

In another embodiment, the sensor 32 may comprise several different sensors. For example, one sensor 32 may sense the vertical acceleration of the padfoot drum (forward) 24 and/or rubber tires (rearward) 22 and a second sensor 32 may detect the vertical acceleration of the compactor frame 12. These sensors 32 may be located proximate to each other but they need not be. Additionally, there may be more than one of each type of sensor 32 located on the compactor machine 11. For example, there may be a sensor 32 sensing the vertical acceleration of the padfoot (forward) drum 24 and a second sensor 32 sensing the vertical acceleration of the rubber tires (rearward) 22 or rear roller drum. While the acceleration of the padfoot drum 24, rubber tires 22, and the compactor frame 12 may be used, the drum acceleration only may be used as the primary signal. Any type of accelerometer may be used as the sensor 32. Such accelerometers include, but are not limited to, laser accelerometers, low frequency accelerometers, bulk micromachined capacitive accelerometers, strain gauge accelerometers, and bulk micromachined piezoelectric accelerometers among others.

According to another embodiment, the sensor 32 may sense force. In such a case, the sensor 32 may be, but is not limited to, a load cell, a strain gauge, or the like. As shown in FIG. 1, the sensor 32 may be located at or close to an axle 30 of the compactor machine 11. In another embodiment, the sensor 32 may be located at or close to the center of frame 12. The transmitted signal may include a sonic signal, an RF signal, or a laser signal, for example, transmitted via a transmitter (not shown) mounted with sensor 32. The sensor 32 may include a non-contact sensor.

In another embodiment, the sensor 32 may comprise a rolling resistance sensor configured to sense a relative rolling resistance of the compaction machine 11 as it moves across the work site. As the compaction machine 11 moves, the energy necessary to propel the machine 11 is generally inversely proportional to the load bearing capacity of the work material Z. In other words, the softer the work material Z, the higher the rolling resistance and the more energy required to propel the compaction machine 11. As the work material Z becomes more compacted, it generally becomes relatively stiffer and less energy is required to move the compaction machine 11.

In one example, the sensor 32 may determine rolling resistance by monitoring the difference between the input to and the output from a torque converter of the compaction machine 11. In such a case, the sensor 32 may include an engine speed sensor for generating signals indicative of the speed or output of the engine and a torque converter speed sensor that monitors the output speed of the torque converter 14. During operation of the compaction machine 11, a difference between the output speed of the engine and the output speed of the torque converter may be used to determine the difference between the input to and the output from the torque converter. If a hydrostatic transmission is used, the sensor 32 may be configured to sense differential pressure. For greater accuracy, the controller 40 may be configured to take into consideration the inclination of the work surface at the particular region of interest when determining the rolling resistance. Such information may be provided by an inclinometer or by the location sensor 46. The controller 40 may use the sensed inclination of the work surface 102 to equate the energy necessary to propel the compaction machine 11 to a common inclination or otherwise adjust the calculation to reflect the incline of the work surface.

The compactor machine 11 may also include a vibratory or vibration system (not shown) associated with the padfoot drum (forward) 24, rubber tires (rearward) 22, and/or a roller drum to impart a compacting force onto the work material Z. More specifically, in addition to the force of the compactor machine 11 being applied to the work material Z to apply compressive forces, the vibration system within the padfoot drum (forward) 24, the rubber tires (rearward) 22, and/or a roller drum may operate to apply additional forces to the work material Z. The vibration system may include any type of system that imparts vibrations, oscillations, or other repeating forces through the padfoot drum (forward) 24, the rubber tires (rearward) 22, and/or a roller drum onto the work material Z. The controller may include a phase sensor 33 that may be configured to measure the phase angle of a vibratory force imparted by the padfoot drum (forward) 24, the rubber tires (rearward) 22, and/or a roller drum (not shown) to the ground. The phase may be measured in real time.

The location sensor 46 may be resident on the compaction machine 11 and may be configured to generate position data indicative of a position of the compaction machine 11 in the work site. For example, the location sensor 46 may be configured to receive global or local positioning data used in establishing and tracking geographic position of compactor machine 11 within a work area. In one embodiment, further described herein, data received via the location sensor 46 may be linked with data received from sensor 32 to map position data of the compactor machine 11 received via the location sensor 46 to a desired structural criteria.

The display 48 also may be coupled with the controller 40 to display various data to an operator relating to machine position, ground stiffness, or still other parameters. The display 48 may be located either on the compactor machine 11 (such as positioned in the operator cab 20), located remotely, or may include multiple displays both on the machine and remotely, and may include, but not limited to, cathode ray tubes (CRT), light-emitting diode display (LED), liquid crystal display (LCD), organic light-emitting diode display (OLED) or a plasma display panel (PDP). Such displays can also be a touchscreen and may incorporate aspects of the input device 39. The display 48 may also include a transceiver for communicating over a communication channel.

As illustrated in FIG. 2, the data processor 42 may be coupled to the sensor 32, phase sensor 33, and the location sensor 46. The data processor 42 may be configured to determine, and then output, at least one structural parameter of the work material using the values sensed by the sensor 32 as the compaction machine passes over the work material Z at the work site. The structural parameter may be a parameter expressed in engineering units that reflects a structural property of the work material Z. For example, the structural parameter may be stiffness or modulus of resilience. Another example of a structural parameter that may be determined by the controller is bearing strength of the work material.

Algorithms for determining the structural parameter (e.g., stiffness or modulus of resilience) using the data provided by the sensor 32, as well as other information from other sensors, such as the phase sensor 33, information about the compactor machine 11 and/or about work site, may be stored in the memory 44. The computer readable memory 44 may include random access memory (RAM) and/or read-only memory (ROM). The memory 44 may also store various digital files including the values sensed by sensor 32, phase sensor 33, or location sensor 46. The memory 44 may also store information input from the input device 39. The information stored in the memory 44 may be provided to the processor 42 so that the processor may determine the structural parameter of the work material such as stiffness or modulus of resilience. Examples of processors include computing devices and/or dedicated hardware having one or more central processing units and microprocessors.

To provide a historical record of the structural parameters of the work material determined by the controller 40 during operation of the compactor machine, the controller 40 may be configured to store the determined structural parameters in memory 44. The memory storage for the structural parameters may be on the compaction machine 11, at a remote location, such as at an on-site or offsite management office, or both. Advantageously, the structural parameter determined by the controller 40 may be a parameter in which the design criteria for the work site is defined. For example, the design criteria for the compaction of a work site often is provided by job specifications in engineering units of stiffness or modulus of resilience. Thus, the structural stiffness or modulus of resilience parameters that are determined and collected by the controller 40 during operation of the compaction machine 11 can provide a permanent record for validating the compacting work at a work site against predetermined structural design criteria for a particular work site. In one embodiment, the predetermined structural design criteria for the job site may be input and stored in the memory 44 of the controller 40 and the data processor 42 may be configured to automatically do the validation comparison of the structural parameters collected by the compaction machine 11 with the predetermined structural design criteria and provide information to an operator or other interested person regarding the result of the validation.

Furthermore, work sites frequently comprise multiple layers of work material Z, each of which is to be compacted to different structural criteria. For example, work sites, such as roads or foundational structures, generally have the highest strength materials at the surface with lesser strength materials below. The sub-surface layers of a road or foundational structure may include a base material, a sub-base material and a sub-grade material. With a road, the pavement on top generally has the highest strength. The base material may comprise the level below the pavement and may also be strong, but relatively less so than the pavement level. The sub-base material may be arranged underneath the base layer and may be constructed using available job site materials that are compacted to a strength higher than the sub-grade, but less than the base material. The sub-grade may be the lowest layer and may include virgin work site material that may have been used as a fill material and compacted to a strength less than that of the sub-base.

To accommodate this multilayer structure, the controller 40 may be configured to save the structural parameters determined during operation of the compaction machine 11 in such a manner that each successive layer of material at a work site may be validated against an associated predetermined design criteria for that layer. For example, this may be accomplished by saving the structural parameters determined by the controller 40 with a time stamp, elevation parameter or marker input by an operator from which it can be determined the layer of the work site to which the structural parameter data corresponds.

Figure 3:
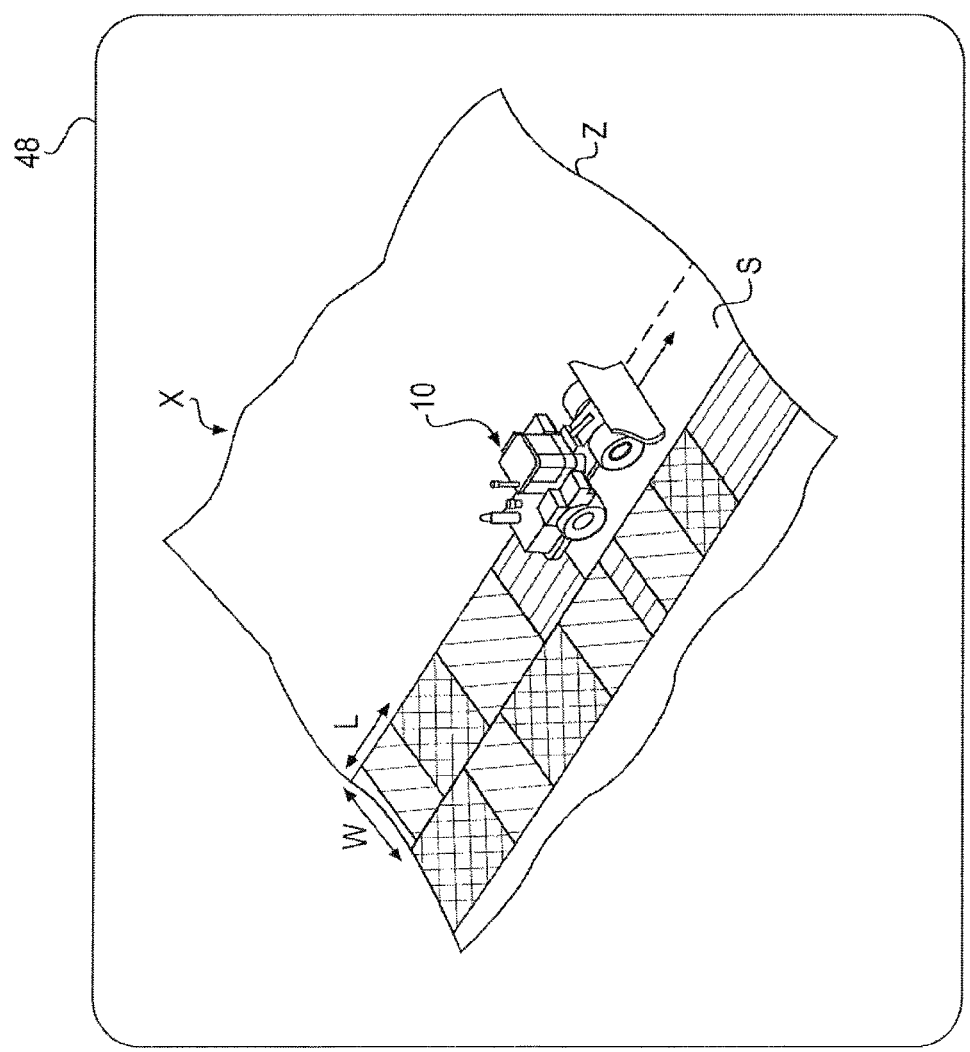
FIG. 3 is a pictorial view of an exemplary display illustrating a mapped compaction state of one layer of a work site.

The controller 40 may be further configured to save in memory 44 the structural parameters determined during operation of the compaction machine 11 in association with position data from the location sensor 46 relating to the location of the compaction machine 11. In this way, a map of the work site may be produced that includes the structural parameters collected by the compaction machine 11 as it passes over the work site. FIG. 3 is an exemplary pictorial view of a display illustrating a map of work site X generated with information from the location sensor 46 and reflecting information regarding the structural parameters collected by the compaction machine 11. In FIG. 3, the work site X has been fragmented into smaller work areas of length L and width W. The smaller work areas have been filled in by different patterns, each of which may correspond to a particular value or range of values of the structural parameter as determined by the controller 40. For instance, the fragmented work areas that have been filled in with horizontal lines may indicate one value or range of values of the structural parameter. The areas that have been filled in with crisscross lines may indicate a different value of range of values of the structural parameters, while the work areas with diagonal lines may indicate areas having a third value or range of values of the structural parameter.

The controller 40 may be configured to save in memory 44 a map, such as shown in FIG. 3, generated from the position data and the structural parameter data. Furthermore, the map may provide the record against which the predetermined design criteria for the work site may be compared for work validation purposes. For work sites having multiple layers of work material, one or more maps, such as shown in FIG. 3, may be saved in memory 44 for each layer of work material during construction at the work site. These maps and/or the underlying data provide information from which the compaction work may be validated against the predetermined design criteria for the work site in three dimensions as well as a permanent record of the construction result in three dimensions.

INDUSTRIAL APPLICABILITY

Figure 4:
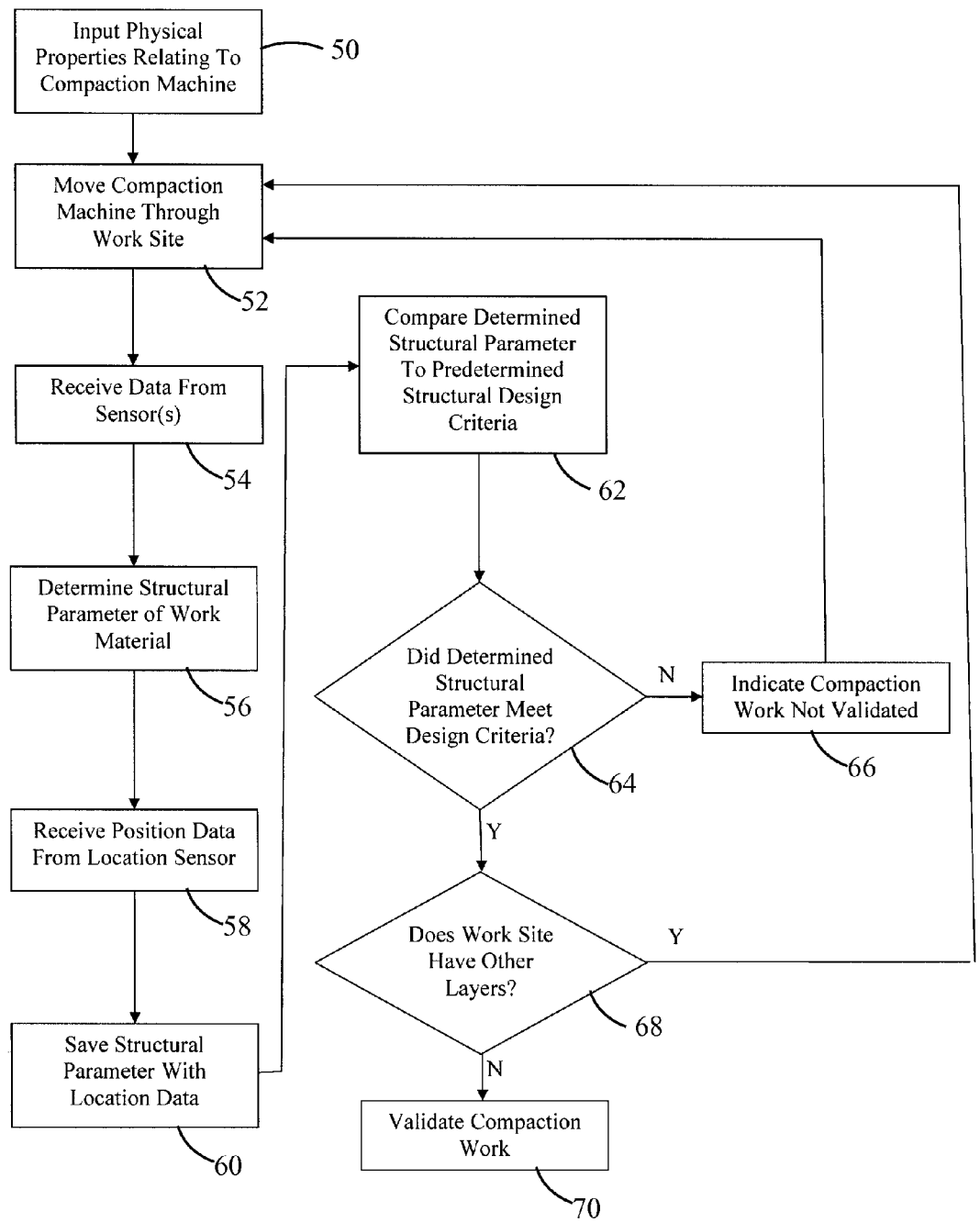
FIG. 4 is a flow chart depicting a method of validating a compaction state of a work site against predetermined structural criteria.

FIG. 4 provides a flow chart of a process for validating the compaction work at a work site against predetermined structural design criteria for the work material at the work site. The process may be implemented, at least in part, by the controller 40 associated with the compaction machine 11. In a step 50, the physical properties of the compaction machine 11 may be stored in the memory 44 associated with the controller 40. The physical properties may be set in a variety of manners such as by entering the model of the compaction machine 11, or by entering a code associated with the machine either electronically (such as with a barcode, an RFID, or the like) or manually. Additionally, the physical properties of the compaction machine 11 may be selected from a database of pre-stored values stored in memory 44 within controller 40 or entered by an operator, management personnel, or other personnel either at the compaction machine 11 or at a location remote from the machine. The physical properties input may include the physical properties of the compactor frame 12, the padfoot drum (forward) 24, and/or a roller drum (not shown). More specifically, the physical properties may include the mass of the padfoot drum (forward) 24 and/or roller drum, the mass of the compactor frame 12 exerted on the padfoot drum (forward) 24 and/or roller drum, the radius and length or width of the padfoot drum (forward) 24 and/or roller drum, and the like. These properties may be constant for a particular compaction machine 11.

In step, 52, the compaction process may begin by moving the compaction machine 11 along a compaction path through the work site. As the compaction machine 11 moves along the compaction path, the controller 40 may receive at step 54 signals or data from the sensor 32 and other sensors associated with the operation of the machine. At step 56, the controller 40 may determine a structural parameter of the work material based on the physical properties of the compaction machine 11 input in step 50 and the data received from the sensor 32 in step 54. The controller 40 may determine the structural parameter on a real-time or near real-time basis as the compaction machine 11 moves through the work site.

The structural parameter of the work material may determined by the controller 40 using any suitable algorithm or relationship. For example, a contact force at an interface between the drum 24 and the work material may calculated using the physical properties of the compaction machine 11 from step 50, data from the sensor 32 including the vertical acceleration of the padfoot drum (forward) 24 and/or roller drum, and the vertical acceleration of the compactor frame 12, and via the phase sensor 33 the vibrational properties, if any, of the padfoot drum (forward) 24 and/or roller drum. The contact force may also be directly sensed by the sensor 32, which may be configured as a force sensor. Once the contact force at the drum-ground interface and the displacement of the padfoot drum (forward) 24 and/or roller drum is calculated, the ground stiffness value and/or the modulus of resilience can be determined. These can be determined using algorithms provided in the controller 40 or via data maps stored within the controller 40. The algorithms may include an iterative process that involves determining a maximum and a minimum roller drum contact force and determining a maximum and a minimum vertical roller displacement. The data maps may be created or determined based upon testing of different compaction machines with different characteristics of the compaction process on different types of materials and at different levels or states of compaction. With a data map, the data communicated by the sensor 32 may be converted by the controller 40 into the structural parameter by looking in the data map for the corresponding value for the structural parameter for the particular data provided by the sensor 32.

At step 58, the controller 40 may receive data relating to the position of the compaction machine 11 from the location sensor 46. The structural parameter determined in step 56 and the corresponding position data from step 58 may be saved together in the memory 44 of the controller 40 in step 60. In some embodiments, the saved data may include a map that graphically relates the position data with the structural parameter determined based on operation of the compaction machine 11. The saved data on the structural parameter and the associated position data can then be compared to the predetermined structural design criteria for that location of the work site in step 62. This comparison is facilitated by the fact that the structural parameter can be the same parameter, with the same units, used in the design criteria. The comparison in step 62 need not be performed on a continuous or real-time basis. For example, the comparison step may not be performed until structural parameters are determined and then saved across the entire work site or a predetermined section of the work site or even until data is collected and saved across multiple layers of a multi-layer work site as described further below.

In decision step 64, if the determined structural parameter meets the design criteria the process may proceed to decision step 68 where it is determined whether the work site is to have multiple layers of work material constructed to different design criteria. If it is to have multiple layers or if the determined structural parameter does not meet the design criteria the process may return to step 52 and the compaction machine may continue to move through the work site and steps 54-68 repeated. In doing so, an indication may be provided in step 66 that the compaction work is not validated. If a different compaction machine is to be used, the process may return to step 52. Once data has been collected on all of the desired layers of the work site and that data has been favorably compared to the design criteria, the process may proceed to step 70 where the compaction work is validated.

Steps 62, 64 and 68 may be performed automatically by the controller if the design criteria is input into the control system as well as information regarding the number of layers of the work site. Alternatively, steps 62, 64 and 68 may be performed manually using a display or other copy of the data saved in step 60.

The present disclosure provides an advantageous system and method for validating the compaction work at a work site against the design criteria. More specifically, instead of providing information about a relative state of compaction that is unitless (e.g., on a 1-100 scale), the system and method of the present disclosure determines structural parameters of the work material, such as stiffness or modulus of resilience. These parameters are the same parameters that are used to define the design criteria for a work site in, for example, job specifications. Thus, the system and method of the present disclosure can collect a historical record of the structural parameter of the work material during operation of the compaction machine that can then be used to validate whether the design has met the specified design criteria for the work site. This can be done with each successive layer of material at a work site. Moreover, because the controller is configured to determine structural parameters of the work material as opposed to a relative state of compaction, it is able to capture the compaction of the work site caused by other machines, such as hauling units, when the compaction machine passes over the work site. As noted above, the system and process of the present disclosure can be applied to any machine that provides compaction of work material at a work site.

It will be appreciated that the foregoing description provides examples of the disclosed system and technique. All references to the disclosure or examples thereof are intended to reference the particular example being discussed at that point and are not intended to imply any limitation as to the scope of the disclosure more generally. All language of distinction and disparagement with respect to certain features is intended to indicate a lack of preference for those features, but not to exclude such from the scope of the disclosure entirely unless otherwise indicated.

Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context.

Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

We claim:
1. A method for validating compaction of a plurality of layers of work material at a work site, the method comprising:
 (a) passing a compaction machine over a first layer of work material at the work site;
 (b) receiving compaction data from a sensor indicative of a state of compaction of the work material as the compaction machine passes over the work material;
 (c) receiving position data from a location sensor indicative of a height and a position of the compaction machine in the work site;
 (d) determining a structural parameter of the work material based on the compaction data and the physical properties of the compaction machine as the machine passes through the work site;
 (e) associating the structural parameter with the position data for the height and the position of the compaction machine in the work site where the compaction data was received;
 (f) collecting structural parameters and associated position data across the work site;
 (g) saving the structural parameters with the associated position data;
 (h) repeating steps (a)-(g) for a second layer of work material at the work site; and
 (i) generating a three-dimensional map of the work site showing the structural parameters and associated position data for different locations in the work site and for different layers of work material in the work site, including a thickness of each layer for different locations.

2. The method of claim 1 further including the step of comparing the saved structural parameters and associated position data with predetermined structural design criteria for corresponding positions and layers in the work site.

3. The method of claim 1 wherein the structural parameter and the predetermined structural design criteria are each expressed as a stiffness.

4. The method of claim 1 wherein the structural parameter and the predetermined structural design criteria are each expressed as a modulus of resilience.

5. The method of claim 1 wherein the at least one sensor is configured to sense at least one of a vertical acceleration, a vertical displacement and a force of a compactor component.

6. The method of claim 1 wherein the at least one sensor is an accelerometer that senses a vertical acceleration of a roller drum.

7. The method of claim 1 wherein the at least one sensor generates signals indicative of a rolling resistance of the compaction machine as it travels across the work site.

8. A system for validating compaction of work material at a work site, the system comprising:
 a compaction machine;
 a sensor carried by the compaction machine for generating compaction data indicative of a state of compaction of the work material as the compaction machine passes over the work material;
 a location sensor associated with the compaction machine for generating position data indicative of a height and a position of the compaction machine in the work site;
 a controller configured to receive compaction data from the sensor and position data from the location sensor and to determine a structural parameter of the work material based on the compaction data and physical properties of the compaction machine, the controller being configured to associate the structural parameter of the work material with the position data for the height and the position of the compaction machine where the compaction data was received, the controller being configured to save structural parameters and associated position data for different locations in the work site and for different layers of work material in the work site and to compare the saved structural parameters and associated position data with predetermined structural design criteria for corresponding locations and layers in the work site; and the controller configured to generate a three-dimensional map of the work site showing the structural parameters and associated position date for different locations in the work site and for different layers of work material in the work site, including a thickness of each layer for different locations.

9. The system of claim 8 wherein the structural parameter and the predetermined structural design criteria are each expressed as a stiffness.

10. The system of claim 8 wherein the structural parameter and the predetermined structural design criteria are each expressed as a modulus of resilience.

11. The system of claim 8 wherein the sensor is configured to sense at least one of a vertical acceleration, a vertical displacement and a force of a compactor component.

12. The system of claim 8 wherein the sensor is an accelerometer that senses a vertical acceleration of a roller drum.

13. The system of claim 8 wherein the sensor generates signals indicative of a rolling resistance of the compaction machine as it travels across the work site.

14. The system of claim 8 wherein the controller is configured to store physical properties of the compaction machine.

15. A compaction machine for validating compaction of work material at a work site, the system comprising:
a roller drum configured to compact the work material;
a sensor carried by the compaction machine for generating compaction data indicative of a state of compaction of the work material as the compaction machine passes over the work material;
a location sensor associated with the compaction machine for generating position data indicative of a height and a position of the compaction machine in the work site;
a controller configured to receive compaction data from the sensor and position data from the location sensor and to determine a structural parameter of the work material based on the compaction data and physical properties of the compaction machine, the controller being configured to associate the structural parameter of the work material with the position data for the height and the position of the compaction machine where the compaction data was received, the controller being configured to save structural parameters and associated position data for different locations in the work site and for different layers of work material in the work site and to compare the saved structural parameters and associated position data with predetermined structural design criteria for corresponding locations and layers in the work site; and the controller configured to generate a three-dimensional map of the work site showing the structural parameters and associated position date for different locations in the work site and for different layers of work material in the work site, including a thickness of each layer for different locations.

16. The compaction machine of claim 15 wherein the structural parameter and the predetermined structural design criteria are each expressed as a stiffness.

17. The compaction machine of claim 15 wherein the structural parameter and the predetermined structural design criteria are each expressed as a modulus of resilience.

18. The compaction machine of claim 15 wherein the sensor is configured to sense at least one of a vertical acceleration, a vertical displacement and a force of a compactor component.

19. The compaction machine of claim 15 wherein the sensor is an accelerometer that senses a vertical acceleration of a roller drum.

20. The compaction machine of claim 15 wherein the controller is configured to store physical properties of the compaction machine.

* * * * *